United States Patent [19]

Nieminen et al.

[11] Patent Number: 4,815,115
[45] Date of Patent: Mar. 21, 1989

[54] METHOD OF PHOTOGRAPHING AN OBJECT WITH A PANORAMIC X-RAY APPARATUS FITTED WITH AUTOMATIC EXPOSURE

[75] Inventors: Tero Nieminen; Timo Nieminen, both of Helsinki, Finland

[73] Assignee: Radiante OY, Helsinki, Finland

[21] Appl. No.: 11,046

[22] Filed: Feb. 5, 1987

[30] Foreign Application Priority Data

Feb. 11, 1986 [FI] Finland .................. 8535/71

[51] Int. Cl.⁴ .............................................. A61B 6/04
[52] U.S. Cl. .................................... 378/38; 378/39; 378/40; 378/108; 378/168
[58] Field of Search .............. 378/38, 39, 40, 108, 378/168

[56] References Cited

U.S. PATENT DOCUMENTS 4,433,430  2/1984  Fredzell .................... 378/108
4,475,224 10/1984  Grassme ................... 378/38

FOREIGN PATENT DOCUMENTS 2650872  5/1978  Fed. Rep. of Germany .
3043632 11/1980  Fed. Rep. of Germany .
  69522  7/1978  Finland .
843039  8/1984  Finland .

Primary Examiner—Carolyn E. Fields
Assistant Examiner—David P. Porta
Attorney, Agent, or Firm—Morse, Altman, Dacey & Benson

[57] ABSTRACT

The invention relates to a method of photographing a desired object with a panoramic X-ray apparatus fitted with automatic exposure, comprising an X-ray generator (4, 5), an X-ray tube (5) and a film (7) with its holder. In the method, the detection of a cone of rays (9) penetrated through an object is effected before the actual filming is started and, after the detection, the filming is effected by using a cone of rays (6), directed so as to bypass a detector (1).

2 Claims, 2 Drawing Sheets

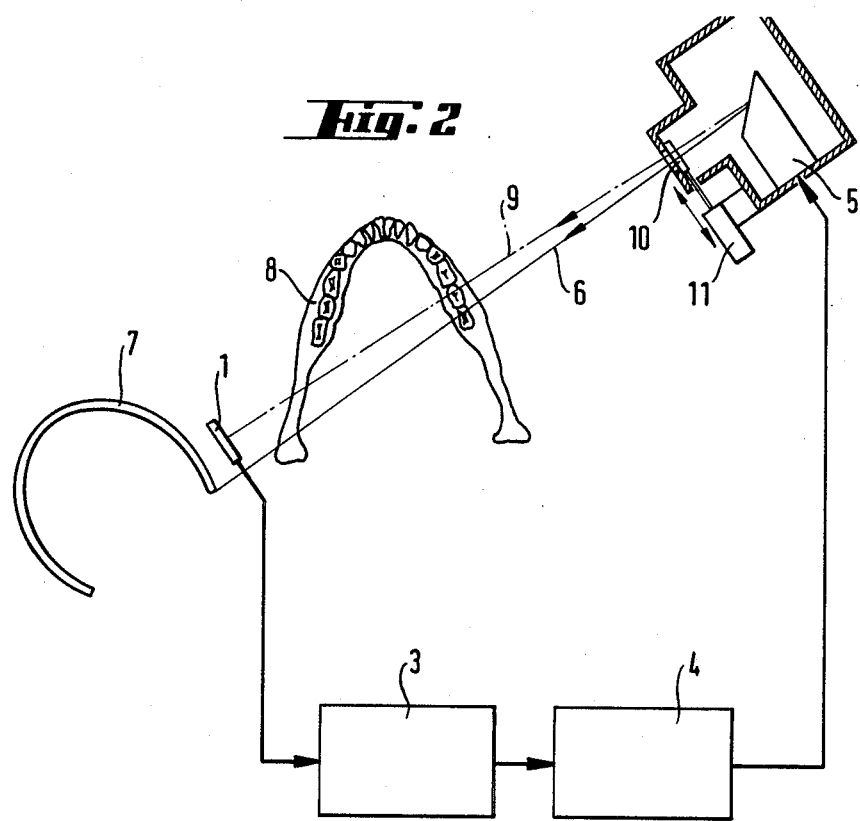
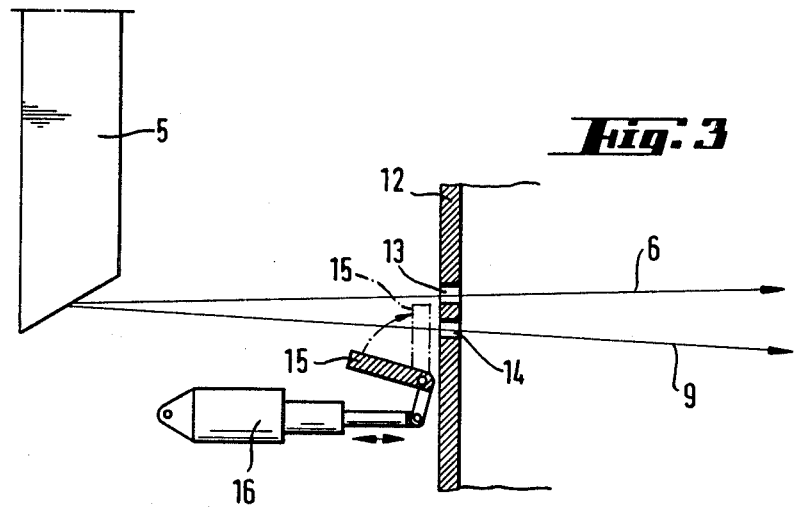

METHOD OF PHOTOGRAPHING AN OBJECT WITH A PANORAMIC X-RAY APPARATUS FITTED WITH AUTOMATIC EXPOSURE

The present invention relates to a method of photographing a desired object with a panoramic X-ray apparatus fitted with automatic exposure, comprising an X-ray generator, an X-ray tube and a film with its holder.

In the use of X-ray equipment, a problem is the selection of proper voltage and current readings in the equipment for an X-ray tube so as to produce a successful dental X-ray image of a patient. Generally, only an experienced operator of the equipment is able to estimate and select proper readings for filming.

A general object of the invention is to provide a photographing or imaging method, wherein the operator need not be capable of selecting the proper readings for filming (kV, mA) for producing a successful dental X-ray image of a patient.

DOS publication discloses how to place the radiation detector of an automatic exposure between an object to be imaged and a film in a manner that the detection of a radiation dosage occurs through the entire filming. In order to avoid showing the detector in the image, it is necessary to employ a specially designed expensive detector, such as an ionization chamber detector.

A particular object of the invention is a further development of the imaging method in a manner that an inexpensive, radiation shielding detector, such as a solid state detector can be placed between an object to be imaged and a film for automatic exposure control.

According to the invention, this object is achieved in a manner that the detection of a cone of rays penetrated through the object is effected prior to starting the actual filming and, after the detection, the filming is effected by using a cone of rays directed so as to bypass the detector.

The invention will now be described in more detail with reference made to the accompanying drawings which illustrate a few embodiments of an apparatus used for carrying out a method of the invention.

FIG. 2 is a block diagram of a second embodiment of an apparatus used for carrying out a method of the invention.

FIG. 3 shows a detail in a third embodiment of an apparatus used for carrying out a method of the invention.

Figure 1:
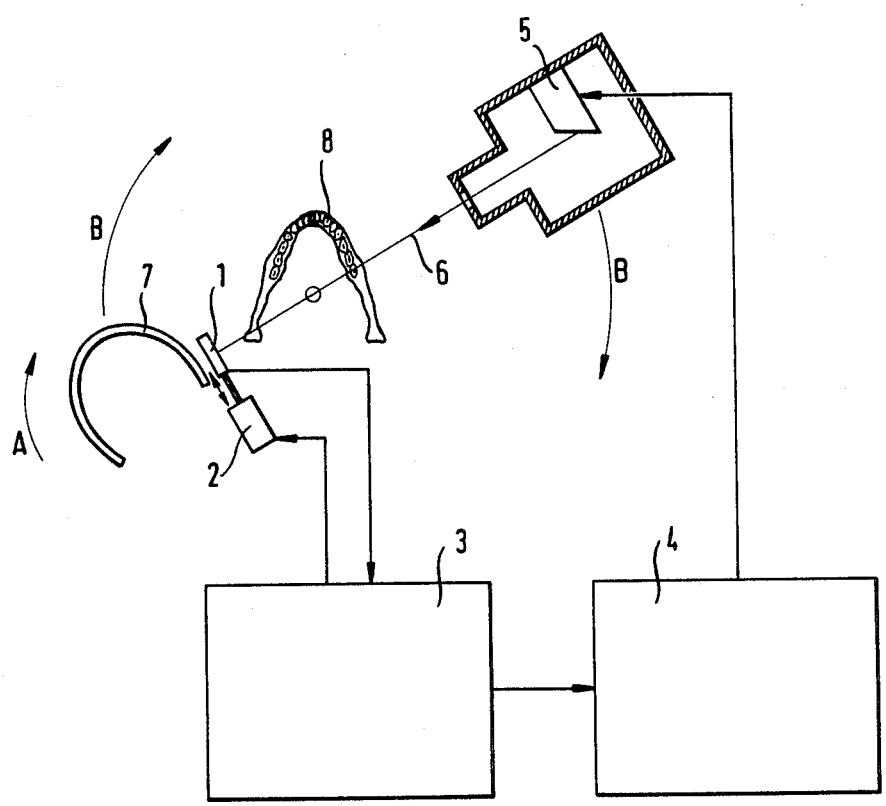
FIG. 1 is a block diagram of a first embodiment of an apparatus used for carrying out a method of the invention.

Since panoramic X-ray methods and equipment are as such generally known and employed, they are not described in detail in this context. As conventional components, the apparatus includes an X-ray generator 4, 5 and an X-ray tube 5 for emitting a cone of X-rays 6 through an object 8 to be imaged onto a film 7. The film 7 is accompanied by conventional reinforcement plates and a film holder, provided with means for driving the film in the direction of an arrow A. The film 7 and its holder are mounted on a frame assembly, which is not shown and is integral with the X-ray tube 5 and can be turned to revolve the film and X-ray tube around the filmed object 8 is the direction of arrows B.

The path of a cone of X-rays 6 penetrated through a filmed object is provided with a radiation measuring detector 1 only before the start of actual filming. In the case of FIG. 1, said detector 1 is coupled with a mechanical detector carrier means 2. Detector 1 is connected to a reference and control unit 3 which, in turn, is adapted to control carrier means 2 and X-ray generator 4.

The voltage and current supplied by X-ray generator 4, 5 to X-ray tube 5 are independently controllable. At the outset of filming, a certain pair of voltage and current readings, e.g. 60 kV and 10 mA respectively, is set in the apparatus. At the outset of filming, the X-ray apparatus runs a survey on a patient with X-rays, whose penetration and intensity are based on said preset pair of kV and mA readings. A detector 1 in the path of a cone of rays supplies information about how much radiation got through the patient. This measured reading is compared in reference and control unit 3 with a reading on which the film darkens properly. A reading, on which the film darkens properly, has been found out empirically. This reading is here called a reference reading. The reference reading is also affected by an employed combination of film/ reinforcement plate, which requires a preadjustment of the reference reading (density).

If a reading measured by detector 1 is lower than the reference reading, the voltage on X-ray tube 5 is increased as required by the difference between these readings. If a measured reading is higher than the reference reading, the amount of radiation is decreased by cutting down the current (mA) passing through the X-ray tube as required by the difference between the measured reading and reference reading.

When measuring and adjustment are completed, said carrier means 2 pulls detector 1 away from the cone of X-rays 6, allowing the rays through to expose the film for the start of actual filming. This measuring and adjustment stage takes appr. 200 ms. The pair of readings used in filming remains visible in X-ray generator 4, 5.

The embodiment of FIG. 2 differs from FIG. 1 in that a radiation measuring detector 1 is stationary and a cone of rays or beam limiting shutter 10 is shifted in a direction perpendicular to the cone of rays. The carrier means of shutter 10 is designated with reference numeral 11 and it can be realized e.g. by using an electromagnet. Before the filming is started, said carrier means 11 shifts the limiting shutter 10 to a position wherein a cone of rays limited thereby falls on detector 1. When the time needed for the operation of automatic exposure has lapsed, e.g. 150 ms, said carrier means 11 shifts shutter 10 to a filming position wherein the cone of rays 6 falls on film 7.

In the embodiment shown in FIG. 3, a radiation measuring detector is also stationary. A cone of rays or beam limiting shutter 12 is provided with two ray-passing gaps 13, 14. The primary cone of rays 6 passed through the ray-passing gap 13 falls on film and the secondary cone of rays 9 passed through the ray-passing gap 14 does not affect the image. The secondary cone of rays 9 passes through a patient to the detector over a period of time required for measuring, e.g. appr. 150 ms at the outset of filming. Thereafter, the secondary cone of rays 9 is eliminated by turning a shield 15, which is made of lead, in front of the cone of rays 9. The turning mechanism 16 is operated e.g. by an electromagnet.

We claim:

1. A method of photographing a desired object with a panoramic x-ray apparatus fitted with automatic exposure, including an x-ray generator (4, 5), an x-ray tube (5) and a film (7) with its holder, comprising the steps of:

(a) effecting a measured reading of a stationary object (8) via a single cone of rays (6) emanating from said x-ray tube (5) and directed at a detector (1) interposed between said object and said film (7) and blocking said cone of rays (6) from reaching said film (7);

(b) comparing said measured reading to a referenced reading;

(c) adjusting the output of said x-ray tube (5) in view of the comparison in said readings;

(d) removing said detector (1) from the path of said single cone of rays (6);

(e) exposing said film (7) to said single cone of rays (6);

(f) wherein a detector carrier means (2), under the control of a reference and control unit (3), moves said detector (1 out of the way of said cone of rays (6) automatically as soon as said adjusting is completed, and (g) wherein with a measured reading below said referenced reading, the voltage supplied to said x-ray tube, is increased and, with measured reading above said referenced reading, the current passing through said x-ray tube (5) is decreased.

2. A method of photographing a desired object with a panoramic x-ray apparatus fitted with automatic exposure, including an x-ray generator (4, 5), an x-ray tube (5) and a film (7) with its holder, comprising the steps of:

(a) effecting a measured reading of a stationary object (8) via a first cone of rays (9) generated by said x-ray tube (5) via a movable limiting shutter (10) having but one ray-passing aperture and being in a first position of two operative positions and directed thereby at a stationary detector (1);

(b) comparing said measured reading to a referenced reading;

(c) adjusting the output of said x-ray tube (5) in view of the comparison in said readings;

(d) moving said movable limiting shutter (10) to a second position of said two operative positions so as to allow thereby an angularly shifted second cone of rays (6) to bypass said stationary detector (1) and to effect an exposure of said film (7).

* * * * *